(12) United States Patent
Davis et al.

(10) Patent No.: US 12,280,197 B2
(45) Date of Patent: Apr. 22, 2025

(54) VACUUM DRAINAGE COLLECTION BOTTLE

(71) Applicant: Merit Medical Systems, Inc., South Jordan, UT (US)

(72) Inventors: Ryan Davis, Centerville, UT (US); Robert Bilgor Peliks, San Francisco, CA (US); Alex Singleton, Sandy, UT (US); Michael Dean Haslam, Sandy, UT (US); Michael Hallisey, Old Saybrook, CT (US); Jim Mottola, West Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 17/473,771

(22) Filed: Sep. 13, 2021

(65) Prior Publication Data

US 2022/0080097 A1 Mar. 17, 2022

Related U.S. Application Data

(60) Provisional application No. 63/168,383, filed on Mar. 31, 2021, provisional application No. 63/078,105, filed on Sep. 14, 2020.

(51) Int. Cl.
*A61M 1/00* (2006.01)

(52) U.S. Cl.
CPC ....... *A61M 1/60* (2021.05); *A61M 2205/3331* (2013.01); *A61M 2205/583* (2013.01); *A61M 2210/1017* (2013.01); *A61M 2210/1021* (2013.01)

(58) Field of Classification Search
CPC ............ A61M 1/60; A61M 2205/3331; A61M 2205/583; A61M 2210/1017; A61M 2210/1021
USPC ......................................................... 604/319
See application file for complete search history.

(56) References Cited

U.S. PATENT DOCUMENTS

| 2,672,141 | A | | 3/1954 | Filger |
|---|---|---|---|---|
| D202,299 | S | | 9/1965 | Karr et al. |
| 3,334,628 | A | | 8/1967 | Saemann et al. |
| 3,376,991 | A | * | 4/1968 | Deaver ................ B65D 50/046 |
| | | | | 215/217 |
| 3,690,497 | A | | 9/1972 | Lecinski |
| 3,833,000 | A | | 9/1974 | Bridgman |

(Continued)

FOREIGN PATENT DOCUMENTS

| CN | 205031619 | 2/2016 |
|---|---|---|
| EP | 0381123 A1 | 8/1990 |
| WO | 2004056408 | 7/2004 |

OTHER PUBLICATIONS

International Search Report and Written Opinion dated Jul. 15, 2022 for PCT/US2022/022394.

(Continued)

*Primary Examiner* — Andrew J Mensh
(74) *Attorney, Agent, or Firm* — Dorsey & Whitney LLP

(57) ABSTRACT

Devices, systems, and methods used to drain a body cavity under a vacuum are disclosed. The devices include a vacuum container and a cap. The container includes an ergonomic gripping portion to allow a user to easily handle the container in use. The cap includes a sealing member configured to selectively seal an inlet to control the flow of drainage fluid into the vacuum container.

20 Claims, 10 Drawing Sheets

(56) References Cited

U.S. PATENT DOCUMENTS

| | | | |
|---|---|---|---|
| 3,939,835 A | 2/1976 | Bridgman | |
| 3,946,739 A * | 3/1976 | Berman | A61M 1/66 |
| | | | 604/128 |
| 4,063,556 A | 12/1977 | Thomas et al. | |
| 4,178,932 A | 12/1979 | Ryder et al. | |
| 4,376,439 A * | 3/1983 | Lauterjung | A61M 1/66 |
| | | | 600/573 |
| D280,707 S | 9/1985 | Imanishi | |
| D291,179 S | 8/1987 | Frizon | |
| 4,820,284 A | 4/1989 | Hauri | |
| 4,852,753 A | 8/1989 | Ochs | |
| 4,944,724 A | 7/1990 | Goldberg et al. | |
| 5,246,142 A * | 9/1993 | DiPalma | B65D 25/087 |
| | | | 222/129 |
| D375,559 S | 11/1996 | Baxter | |
| 5,803,282 A | 9/1998 | Chen et al. | |
| 5,921,419 A * | 7/1999 | Niedospial, Jr. | B65D 51/002 |
| | | | 215/247 |
| D423,360 S | 4/2000 | Togasawa et al. | |
| 6,056,730 A | 5/2000 | Greter | |
| D449,228 S | 10/2001 | Nosella | |
| 7,048,724 B2 | 5/2006 | Grossman et al. | |
| D547,197 S | 7/2007 | Hermel | |
| D557,606 S | 12/2007 | Rashid | |
| D610,019 S | 2/2010 | Navarro et al. | |
| D632,576 S | 2/2011 | Hermel | |
| D702,556 S | 4/2014 | Quasters | |
| D703,058 S | 4/2014 | Baschmakoff et al. | |
| D747,967 S | 1/2016 | Domènech | |
| D763,699 S | 8/2016 | Rasgon | |
| D763,700 S | 8/2016 | Rasgon | |
| D809,391 S | 2/2018 | Funk | |
| D833,874 S | 11/2018 | Harrison et al. | |
| D948,708 S | 4/2022 | Zhang | |
| 2002/0088131 A1 * | 7/2002 | Baxa | A61M 5/31556 |
| | | | 33/494 |
| 2007/0203463 A1 | 8/2007 | Salvadori et al. | |
| 2009/0110777 A1 | 4/2009 | Buisson | |
| 2010/0181276 A1 | 7/2010 | Brown et al. | |
| 2011/0303670 A1 * | 12/2011 | Baker | B65D 51/002 |
| | | | 220/257.1 |
| 2012/0000878 A1 * | 1/2012 | Reisig | B65D 1/023 |
| | | | 215/40 |
| 2013/0233822 A1 * | 9/2013 | Aneas | B65D 41/28 |
| | | | 215/320 |
| 2015/0065969 A1 | 3/2015 | Stinson | |
| 2021/0009302 A1 * | 1/2021 | Kim | A61J 1/03 |
| 2022/0008650 A1 * | 1/2022 | Arinobe | A61M 5/172 |
| 2022/0080097 A1 | 3/2022 | Davis et al. | |
| 2022/0313552 A1 | 10/2022 | Hallisey et al. | |

OTHER PUBLICATIONS

Notice of Allowance dated Oct. 19, 2022 for U.S. Appl. No. 29/776,580.
Office Action dated Jul. 11, 2022 for U.S. Appl. No. 29/776,580.
"Ward-System", Online, publication date unknown. Retrieved on Jun. 26, 2022 from URL: https://www.pfmmedical.con/productcatagogue/high_vacuum_drainage/ward_system/index.html.
International Search Report and Written Opinion dated Jan. 3, 2022 for PCT/US2021/050132.
Serifinity; B. Braun Interventional Accel Spin-Lock Connection Set—470190, www.serifinitymedical.com/products/accel-spin-lock-connection-set-b-braun-inverventional-470190-929628?variant=3077122872139 Accessed Oct. 12, 2020.
Office Action dated Nov. 7, 2023 for U.S. Appl. No. 17/657,088.
Office Action dated May 10, 2024 for U.S. Appl. No. 17/657,088.
European Search Report dated Sep. 12, 2024 for EP21867786.2.
Office Action dated Oct. 11, 2024 for U.S. Appl. No. 17/657,088.
European Search Report dated Jan. 16, 2025 for EP22782043.8.

* cited by examiner

VACUUM DRAINAGE COLLECTION BOTTLE

RELATED APPLICATIONS

This application claims priority to U.S. Provisional Application No. 63/078,105, filed on Sep. 14, 2020 and titled "Vacuum Drainage Collection Bottle," and U.S. Provisional Application No. 63/168,383, filed on Mar. 31, 2021 and titled "Vacuum Drainage Collection Bottle," each of which is hereby incorporated by reference in its entirety.

TECHNICAL FIELD

The present disclosure relates generally to devices used to drain a cavity of a patient, particularly in medical devices. More specifically, the present disclosure relates to vacuum drainage bottles.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
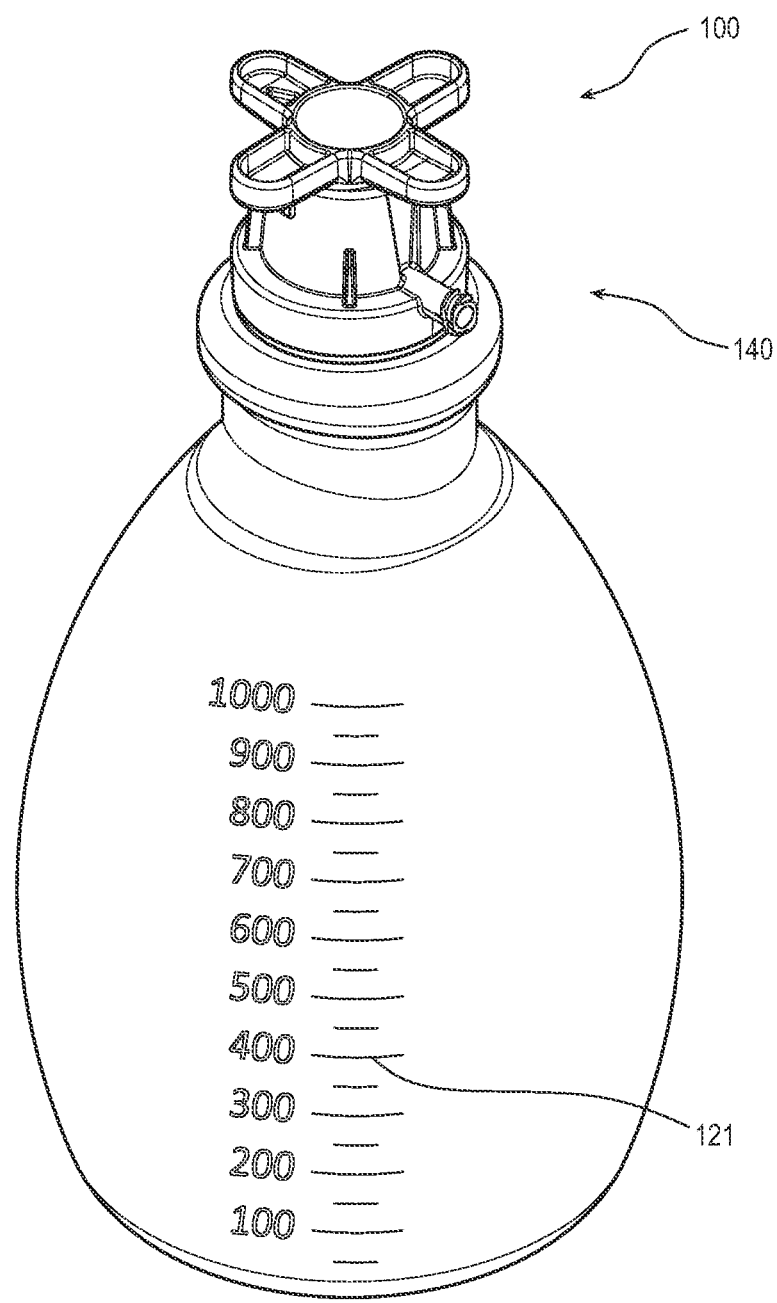
FIG. 1 is a top perspective view of an embodiment of a vacuum drainage collection bottle.

In some instances, body fluids may need to be withdrawn from a patient in the course of medical treatment. For example, two medical procedures requiring fluid removal are thoracentesis and paracentesis. In paracentesis, peritoneal fluid is aspirated from the abdomen. In thoracentesis, pleural fluid is aspirated from the thoracic cavity. In certain instances, paracentesis and thoracentesis have been observed to provide quick and effective relief with few adverse side effects. Relatively large volumes of fluid, such as five liters, may be withdrawn from a patient during a single procedure. The paracentesis and thoracentesis procedures can be conducted in a health care facility by healthcare workers or in a patient's home by the patient. Many existing devices are capable of performing paracentesis and thoracentesis. At its simplest, a paracentesis or thoracentesis device need only include a hollow needle with one end inserted into the patient and the other end attached to a negative gauge pressure or vacuum device, such as a vacuum drainage collection bottle.

A vacuum drainage collection bottle of the present disclosure includes a truncated football shape container that is provided to a user with an internal negative gauge pressure or vacuum. Containers within the scope of this disclosure can have a broad base and a low center of gravity to reduce a risk of the container tipping over and spilling the collected drainage fluid. In some embodiments within the scope of this disclosure, a neck portion of the container may have an oval transverse cross-sectional shape with a major axis greater than a minor axis. A flange may be disposed at the top of the neck portion and extend radial outwardly from the neck portion. Both the oval shape and the flange of the neck portion may provide an ergonomic grip to allow a user to easily handle the vacuum drainage collection bottle at any point of filling or emptying.

In certain embodiments within the scope of this disclosure, a cap may be connected to the container. The cap can have a body with an inlet in fluid communication with the container. In some embodiments, the inlet may include an external connector for connection of a drainage tube. Caps within the scope of this disclosure can include internal threads that are configured to engage with external threads of a plunger of a sealing member. In certain embodiments, the sealing member may include a stopper that selectively seals the inlet to prevent passage of fluid or gas through the inlet. The stopper may be displaced from a closed state to an open state by threadingly rotating or otherwise unthreading the plunger with a plunger handle. In the open state the stopper may be displaced away from the inlet such that fluid is drawn into the container by the vacuum or negative gauge pressure within the container.

In some embodiments within the scope of this disclosure, a rate of fluid flow into the container can be controlled by partial displacement of the stopper from the inlet such that only a portion of the inlet is open and in fluid communication with the container. In certain embodiments, the fluid flow can be stopped prior to an end of a drainage procedure by threadingly rotating the plunger in a second direction to displace the stopper toward the inlet and seal the stopper against the inlet. In some embodiments, drainage fluid can be removed from the container by threadingly removing or unthreading the sealing member from the cap to provide a large opening through the cap.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

"Fluid" is used in its broadest sense, to refer to any fluid, including both liquids and gases as well as solutions, compounds, suspensions, etc., which generally behave as fluids.

FIGS. 1-9B illustrate different views of various embodiments of a vacuum drainage collection bottle and related components. In certain views the vacuum drainage collection bottle may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Figure 2:
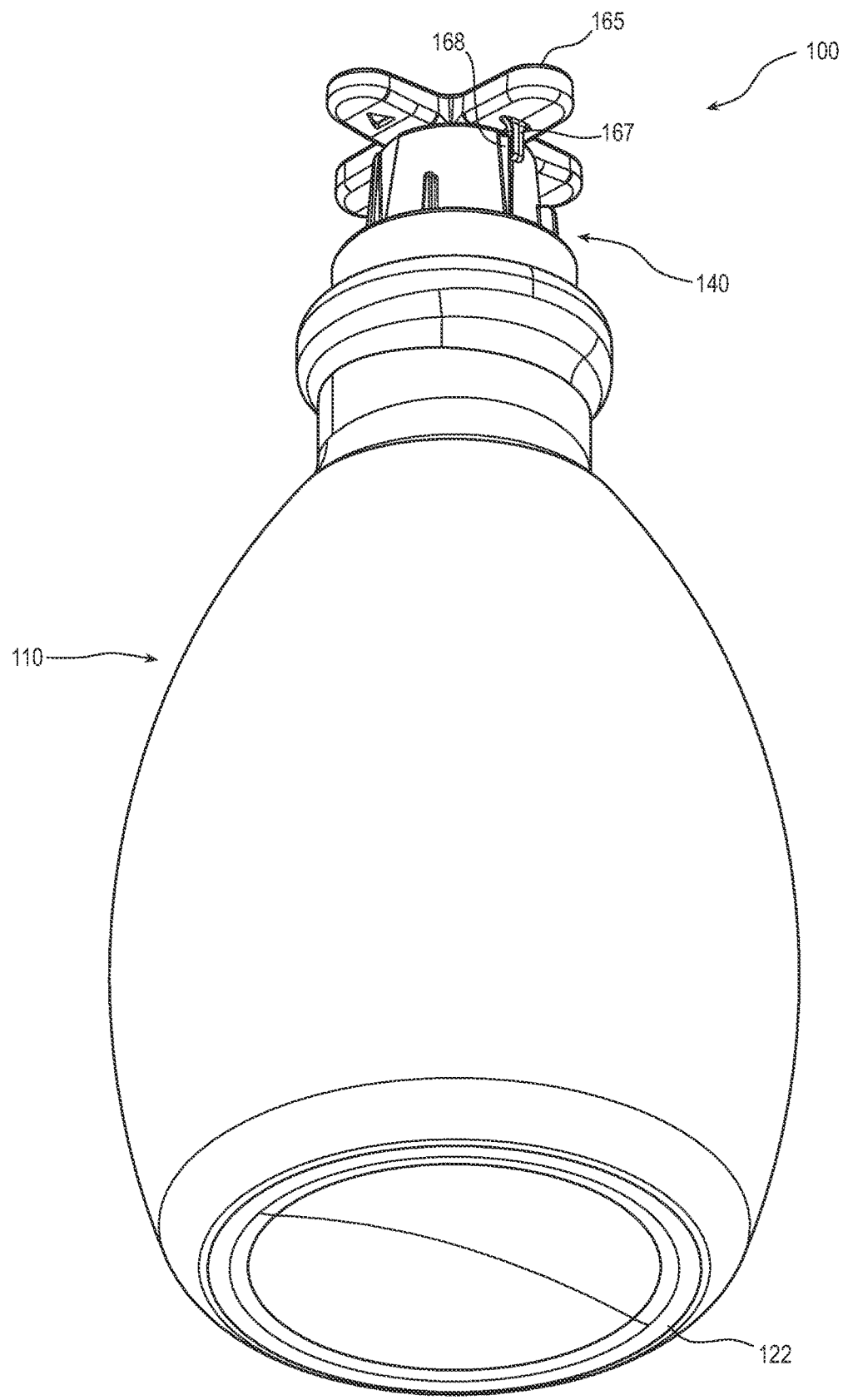
FIG. 2 is a bottom perspective view of the vacuum drainage collection bottle embodiment of FIG. 1 rotated 180 degrees.
Figure 3:
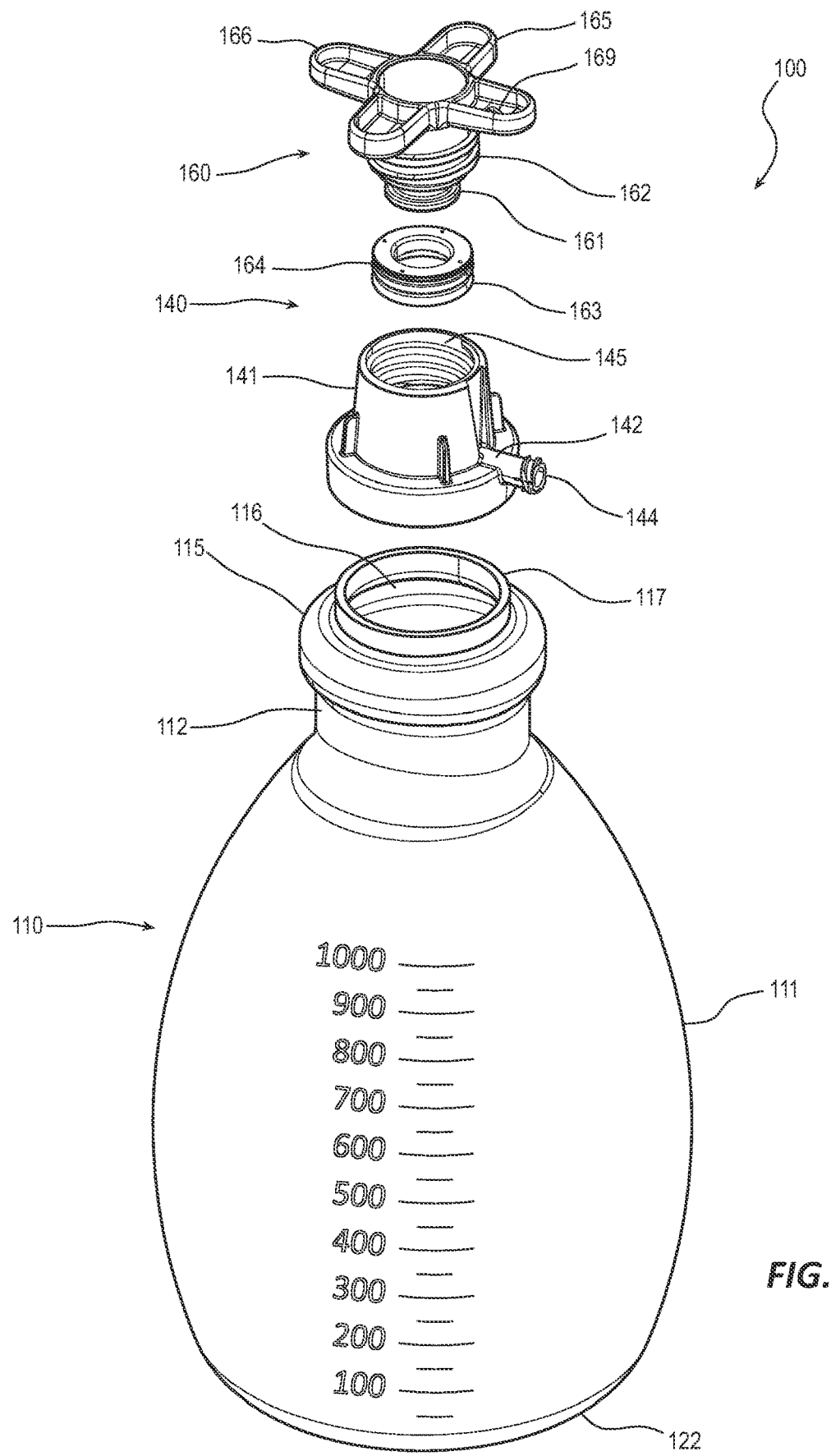
FIG. 3 is an exploded perspective view of the vacuum drainage collection bottle embodiment of FIG. 1.
Figure 4A:
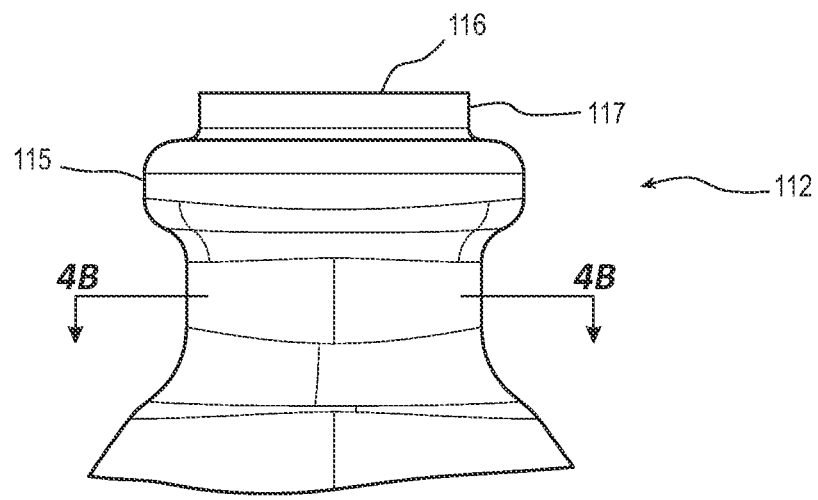
FIG. 4A is a side view of a neck portion of the vacuum drainage collection bottle embodiment of FIG. 1.
Figure 4B:
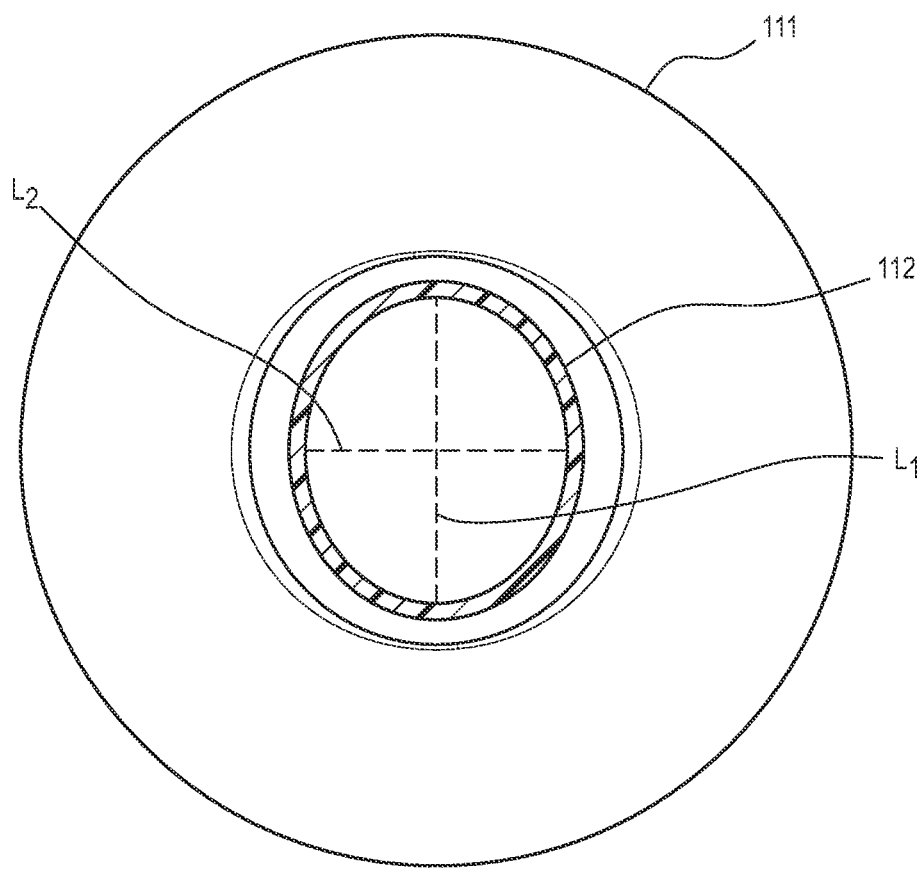
FIG. 4B is a transverse cross-sectional top view of the neck portion of FIG. 4A.
Figure 5A:
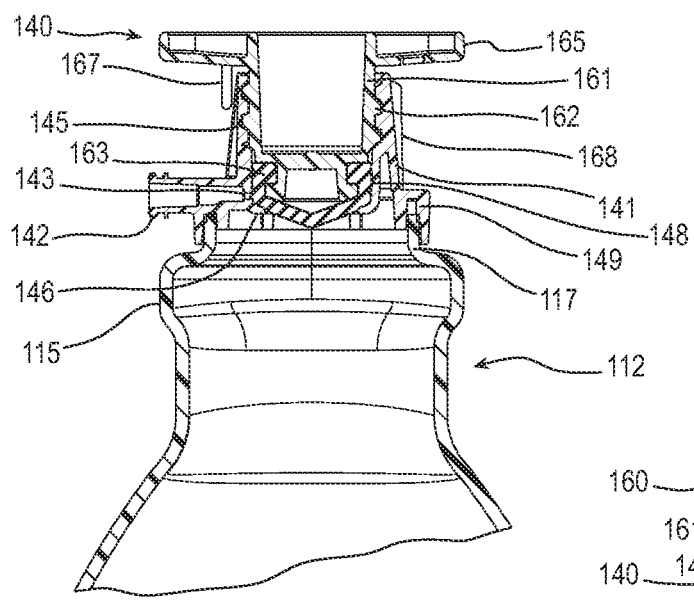
FIG. 5A is a longitudinal cross-sectional view of a cap of the vacuum drainage collection bottle embodiment of FIG. 1 in a closed state.
Figure 5B:
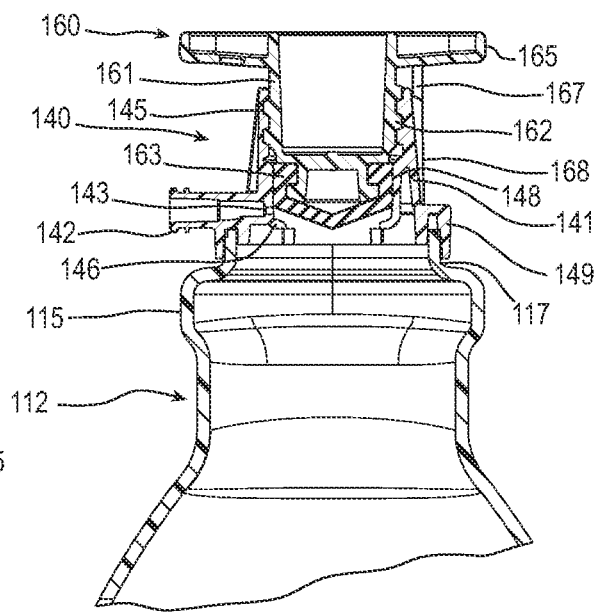
FIG. 5B is a longitudinal cross-sectional view of the cap of the vacuum drainage collection bottle embodiment of FIG. 1 in an open state.
Figure 5C:
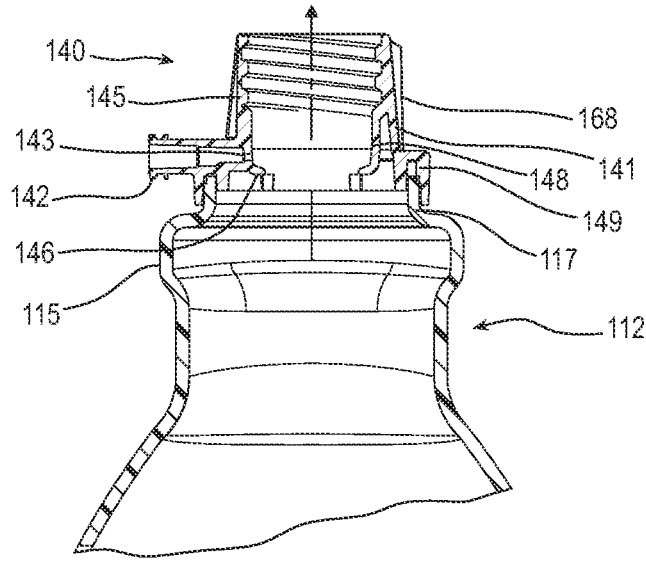
FIG. 5C is a longitudinal cross-sectional view of the cap of the vacuum drainage collection bottle embodiment of FIG. 1 with a sealing member removed from the cap.
Figure 6:
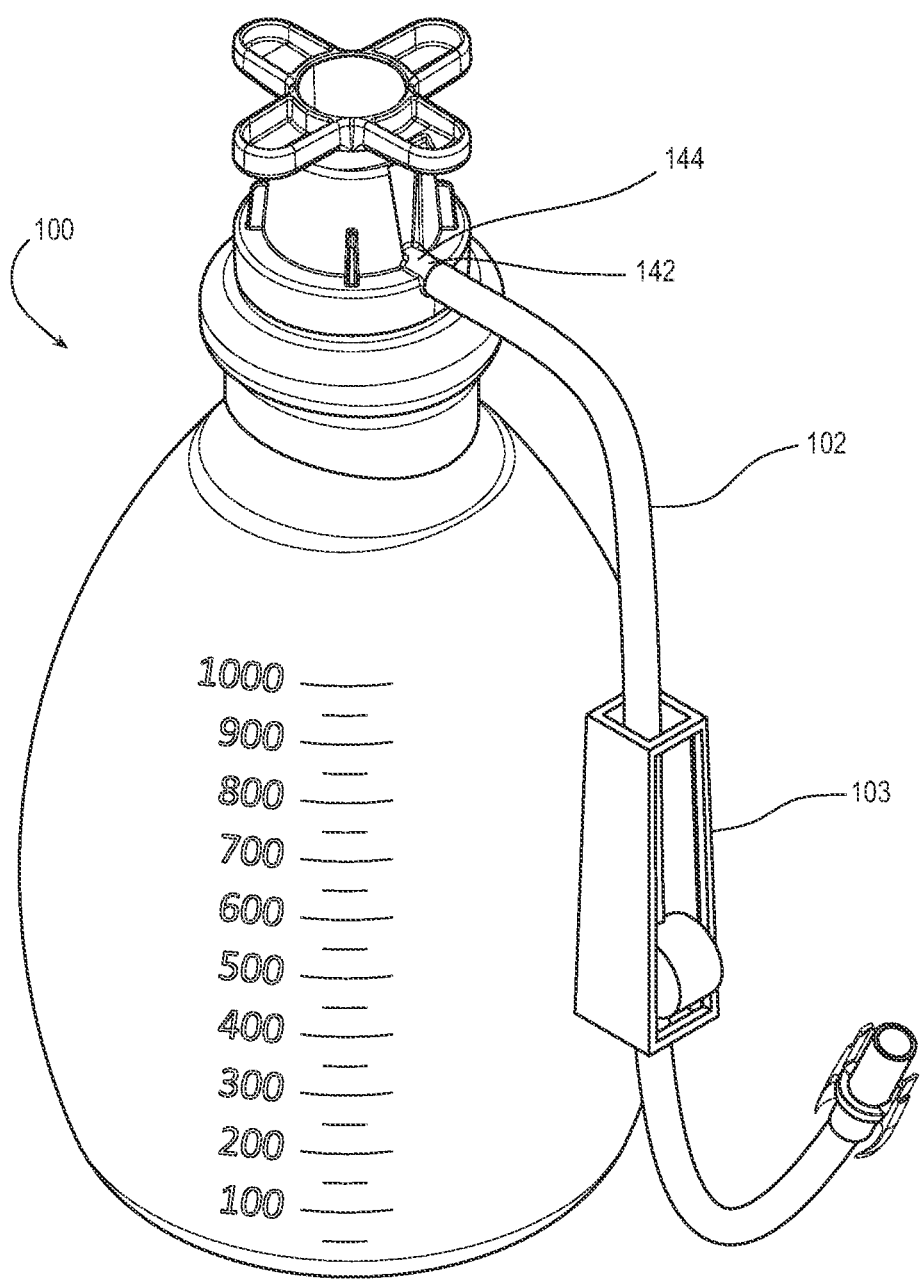
FIG. 6 is a perspective view of the vacuum drainage collection bottle embodiment of FIG. 1 with a drainage tube coupled to an inlet.
Figure 7:
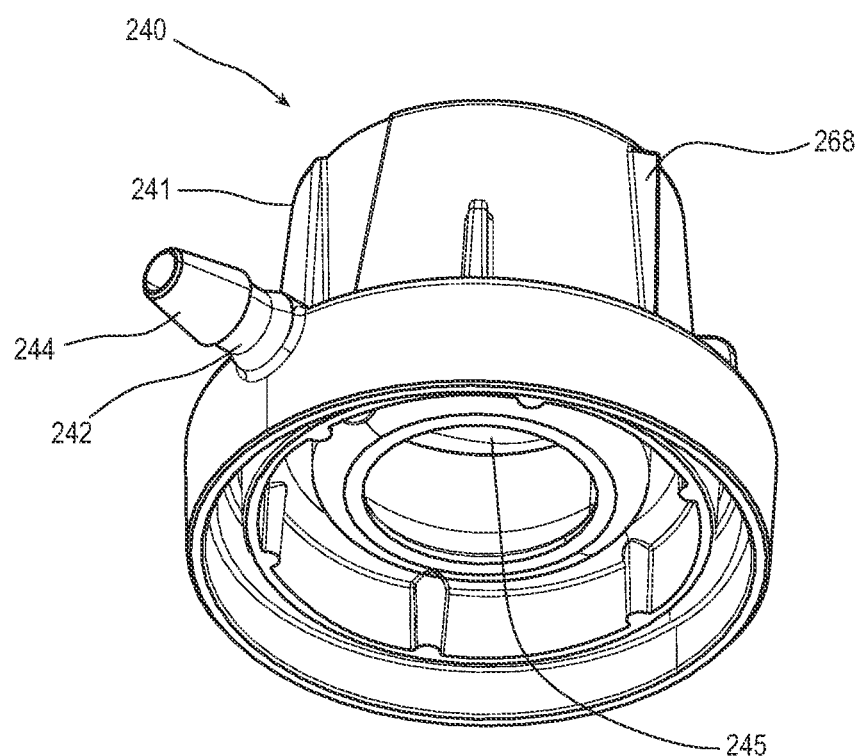
FIG. 7 is a perspective view of another embodiment of a body of a cap including a barbed external connector.
Figure 8:
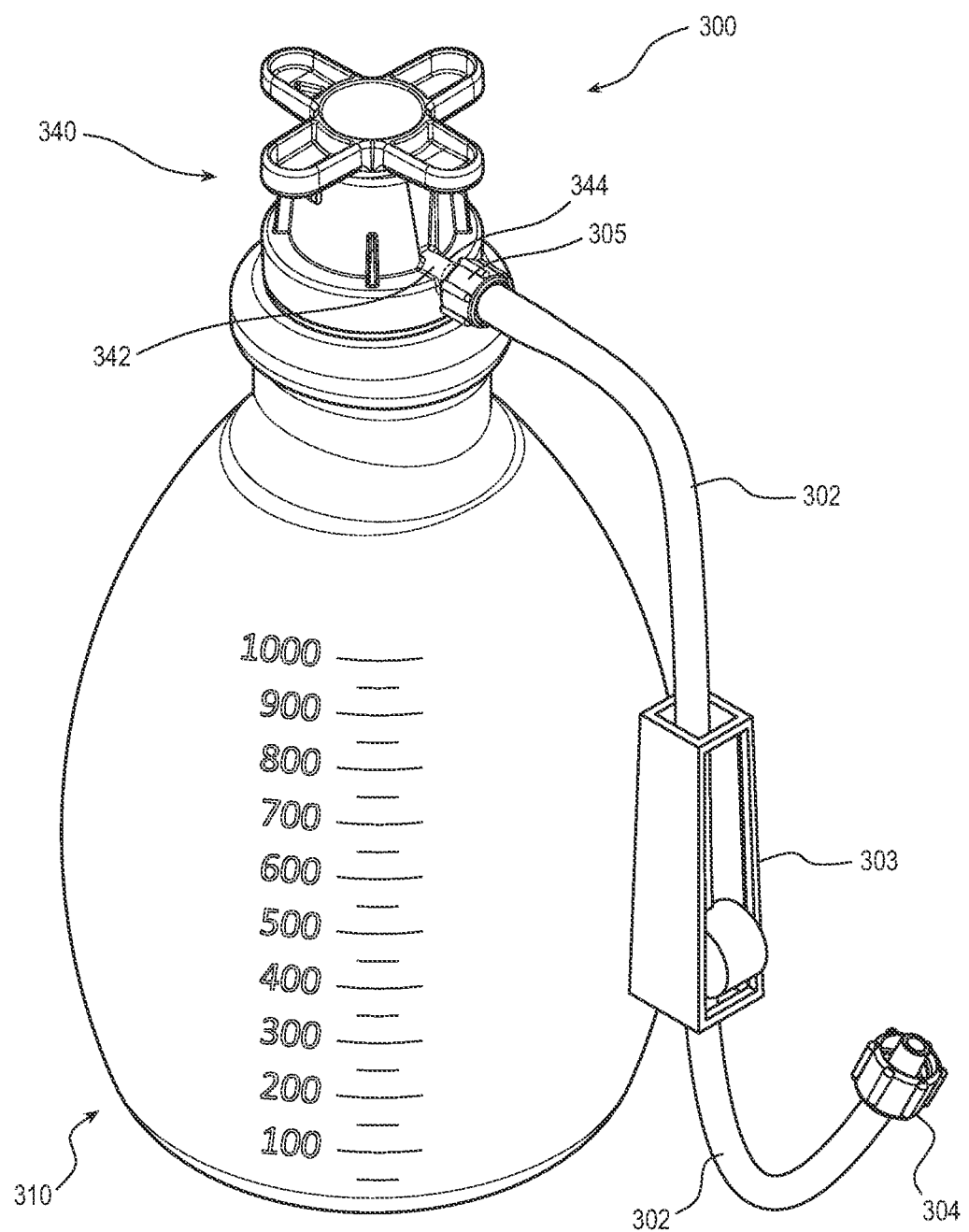
FIG. 8 is a perspective view of another embodiment of a vacuum drainage collection bottle including a male Luer-male Luer drainage tube.

FIGS. 1 and 2 illustrate an embodiment of a vacuum drainage collection bottle. FIG. 3 illustrates an exploded view of the vacuum drainage collection bottle of FIG. 1. FIGS. 4A and 4B illustrate a neck portion of the vacuum drainage collection bottle of FIG. 1. FIGS. 5A, 5B, and 5C illustrate an embodiment of a cap of the vacuum drainage collection bottle of FIG. 1. FIG. 6 illustrates an embodiment of a drainage tube coupled to a vacuum drainage collection bottle. FIG. 7 illustrates another embodiment of a cap of a vacuum drainage collection bottle. FIG. 8 illustrates another embodiment of a vacuum drainage collection bottle including a male Luer-male Luer drainage tube.

In the illustrated embodiment of FIGS. 1 and 2, the vacuum drainage collection bottle 100 includes two broad groups of components; each group may have numerous subcomponents and parts. The two broad component groups are: a receptacle or container 110 and a cap 140. As shown in FIG. 2, the cap 140 can include a rotation stop rib 168 and a handle 165 having a rotation stop protrusion 167 configured to engage the rotation stop rib 168. The function of the rotation stop protrusion and rib 167, 168 will be discussed below.

FIG. 3 is an exploded perspective view of the drainage collection bottle embodiment 100. As illustrated in FIG. 3, the container 110 may include a body (or drainage containment) portion 111 and a neck portion 112. The body portion 111 may be a hollow object, which in some embodiments is formed from a transparent, translucent, or opaque, rigid or semi-rigid material, such as glass, plastic, polymeric materials, polycarbonate, polyesters, cyclic olefin copolymers, etc., using any suitable manufacturing technique, such as molding, blow molding, glass blowing, etc. The body portion 111 may include indicia 121, shown in FIG. 1, to indicate a volume of collected drainage fluid. The indicia 121 can also be included or printed on a shrink wrap or shrink sleeve that is applied to the container 110. Additional indicia 121, labeling, and/or coloring can also be included on a shrink wrap or shrink sleeve, or can be otherwise printed on the container 110. In the illustrated embodiment of FIG. 3, the body portion 111 may have a truncated prolate spheroid shape or truncated football shape with a broad base 122 (also shown in FIG. 2). A diameter of the base 122 can range from about 65% to about 85%, or about 70%, relative to a largest diameter of the body portion 111.

The truncated prolate spheroid shape of the body portion 111 can provide a low center of gravity for the vacuum drainage collection bottle 100. The center of gravity of the vacuum drainage collection bottle 100 can range from about 25% to about 45% of a height of the container 110 when the vacuum drainage collection bottle 100 is empty. In other embodiments, the center of gravity of the vacuum drainage collection bottle 100 is less than about 45% of a height of the container 110 when the vacuum drainage collection bottle 100 is empty. In yet other embodiments, the center of gravity of the vacuum drainage collection bottle 100 is about 33% of a height of the container 110 when the vacuum drainage collection bottle 100 is empty. In combination, the base 122 of the body portion 111 and the low center of gravity of the vacuum drainage collection bottle 100 can provide for stability of the vacuum drainage collection bottle 100 to help prevent the vacuum drainage collection bottle 100 from tipping over during use and spilling its contents. In some embodiments, other features in combination with broad base 122 and the low center of gravity of the vacuum drainage collection bottle 100 may provide stability to the vacuum drainage collection bottle 100. For example, the vacuum drainage collection bottle 100 may include a base ring or flange extending radial outward from the base 122. In other embodiments that are within the scope of this disclosure, the body portion 111 may have any other suitable cross-sectional shape. For example, a cross-sectional shape of the body portion 111 may be round, square, an outwardly tapered cylinder with a broad base, etc.

In the embodiment of the vacuum drainage collection bottle 100 illustrated in FIG. 3, the neck portion 112 can extend upward from and be in fluid communication with the body portion 111. The neck portion 112 can include a hollow tube having a non-round cross-sectional shape. FIG. 4A is a side view of the neck portion 112 and FIG. 4B is a transverse cross-sectional view of the neck portion 112. In the depicted embodiment of FIGS. 4A and 4B, the neck portion 112 may have an oval cross-sectional shape with a length of a primary axis $L_1$ greater than a length of a secondary axis $L_2$. In some embodiments, a ratio of the length of the primary axis $L_1$ to the secondary axis $L_2$ may range from about 1.05:1 to about 1.35:1, or may be about 1.15:1. In other embodiments within the scope of this disclosure, the neck portion 112 may include any other suitable non-round cross-sectional shape, such as elliptical, square with rounded corners, rectangular, etc. In yet further embodiments, the neck portion 112 may include a substantially round cross-sectional shape. In some embodiments, the neck portion 112 may include finger grips to facilitate handling of the vacuum drainage collection bottle 100.

In certain embodiments, the non-round shape (e.g., oval shape) of the neck portion 112 may be configured to provide an ergonomic grip for users of the vacuum drainage collection bottle 100. In certain instances, users of the vacuum drainage collection bottle 100 are older in age and may have weakened hand strength. The oval shape of the neck portion 112 may allow the user to easily grip and handle the vacuum drainage collection bottle 100 during use. Additionally, the oval shape may provide leverage against rotation of the neck portion 112 when a handle 165 of a cap 140 (shown in FIG. 3) of the vacuum drainage collection bottle 100 is rotated to initiate, stop, or alter a drainage procedure, such as paracentesis or thoracentesis. For example, the user may grip the neck portion 112 with fingers of a first hand such that the fingers are substantially parallel with the primary axis $L_1$ of the neck portion 112. A second hand may rotate the handle 165 in a first direction while the first hand applies a counter rotational force to the neck portion 112 in an opposite direction to prevent the neck portion 112 and the container 110 from rotating in the first direction.

As shown in FIG. 3, a flange 115 can be disposed adjacent an upper portion of the neck portion 112. The flange 115 may extend radial outwardly from the neck portion 112 and have a circular or oval cross-sectional shape. The flange 115 may be configured to facilitate handling of the vacuum drainage collection bottle 100 during use. For example, a user may grip the neck portion 112 with fingers of one hand and lift the vacuum drainage collection bottle 100 when it is filled or partially filled. As mentioned previously, the user may have weakened hand strength and may be unable to grip the neck portion 112 adequately to lift the vacuum drainage collection bottle 100 by friction only. The flange 115 may be supported on the user's fingers and/or hand to facilitate lifting of the vacuum drainage collection bottle 100.

As illustrated in FIG. 3, the neck portion 112 may include a rim 117 and a mouth 116. The rim 117 may be circular and can be used to facilitate coupling of the cap 140 to the container 110. The mouth 116 can be an opening defined by the rim 117 and may be configured to allow drainage fluid to flow into and out of the container 110.

In the embodiment of the vacuum drainage collection bottle 100 illustrated in FIG. 3, the cap 140 includes a body 141. In the illustrated embodiment, the body 141 can include an inlet 142, internal threads 145, and a stopper seal surface 148 (shown in FIG. 5A). The body 141 can be sealingly coupled to the container 110 using any suitable technique. For example, as shown in FIG. 5A, the body 141 may include an annular channel 149 configured to receive the rim 117. The annular channel 149 and the rim 117 may be joined together using heat welding, vibration welding, bonding, gluing, etc. In other embodiments, the body 141 and the container 110 can be coupled by a snap fit, a frictional fit, a threaded coupling, etc. One or more sealing members can also be used.

The inlet 142, as depicted in FIG. 3, may include an external connector 144 and a fluid channel 143 (shown in FIGS. 5A and 5B). The external connector 144 can be of any suitable configuration capable of attachment to a drainage tube. As depicted in FIG. 3, the external connector 144 may be a female Luer lock connector configured to receive a male Luer lock connector. In other embodiments, the external connector 144 may be a barbed connector, as shown in FIG. 7, configured to receive a drainage tube without a connector. The fluid channel 143 may pass through a wall of the body 141 and provide fluid communication between the external connector 144 and the container 110 as shown in FIG. 5B. Other types of external connectors 144 can also be used.

As shown in FIG. 3, the internal threads 145 can be configured to threadingly engage with external threads 162 of the sealing member 160 and the stopper seal surface 148 may be configured to sealingly and slidably couple with a stopper 163 of the sealing member 160, as shown in FIG. 5A.

In the illustrated embodiment of FIG. 3, the sealing member 160 may include a plunger 161, the stopper 163 coupled to an end of the plunger 161, and the handle 165 disposed at end of the plunger 161 opposite the stopper 163. The plunger 161 may include external threads 162 configured to threadingly engage with the internal threads 145 of the body 141.

As depicted in FIG. 3, the stopper 163 may be formed of a compliant material, such as rubber, thermoplastic elastomer, etc. and configured to selectively seal the inlet 142 to prevent passage of drainage fluid through the inlet 142. The stopper 163 may also form a circumferential seal with the stopper seal surface 148 to prevent passage of gas by the stopper 163 to maintain a vacuum within the container 110. In some embodiments, the stopper 163 can include seal rings 164 to provide the circumferential seal with the stopper seal surface 148.

The handle 165 may be configured to rotate the plunger 161 to displace the stopper 163 relative to the fluid channel 143. As depicted in FIG. 3, the handle 165 can include one or more arms 166 (e.g., four arms 166 as illustrated) extending radial outwardly from a central axis of the plunger 161 and spaced circumferentially equidistance. In other embodiments, the number of arms 166 may be 1, 2, 3, 5, or more. In certain embodiments, the handle 165 can include an indicium 169, such as an arrow, to indicate whether the cap 140 is in a closed state or an open state.

FIG. 5A depicts the cap 140 of the vacuum drainage collection bottle 100 in the closed state. In the closed state, as shown in FIG. 5A, the stopper 163 may be disposed against a seal ring 146 of the body 141 such that the stopper 163 can seal the fluid channel 143 of the inlet 142. When sealed, drainage fluid can be prevented from passing through the fluid channel 143 and into the container 110. The stopper 163 can also circumferentially seal against the stopper seal surface 148 to prevent gas from passing by the stopper 163 and reducing the vacuum within the container 110. In the closed state, a rotation stop protrusion 167 may extend downward from the handle 165 and may be positioned about 180 degrees from a rotation stop rib 168 extending radial outwardly from the body 141.

FIG. 5B depicts the cap 140 of the vacuum drainage collection bottle 100 in an open state. The cap 140 can be transitioned to the open state when the handle 165 is rotated in a first direction causing the plunger 161 to rotate. In the open state the stopper 163 may be displaced relative to the fluid channel 143 such that the stopper 163 does not seal the fluid channel 143. When the plunger 161 is rotated, the internal and external threads 145, 162 may engage to displace the plunger 161 and the stopper 163 upward relative to the fluid channel 143. In some embodiments, the handle 165 may be rotated from about one degree to about 180 degrees or more to displace the stopper 163. When the handle 165 is rotated about 180 degrees, the stopper 163 may be displaced upwardly such that the fluid channel 143 is not sealed by the stopper 163 and drainage fluid is allowed to flow freely through the fluid channel 143, which may be caused in part by the vacuum or negative gauge pressure within the vacuum drainage collection bottle 100. When the handle 165 is rotated less than about 180 degrees, the stopper 163 may partially block or seal the fluid channel 143 and drainage fluid flow through the fluid channel 143 may be reduced. It may be advantageous to a patient to selectively reduce the flow of drainage fluid when s/he feels discomfort when the drainage fluid is flowing at a high rate. Further, while rotation of about 180 degrees to open the fluid channel 143 is discussed above, it will be appreciated that the degree of rotation to open and/or close fluid channel 143 can be modified as desired.

In the depicted embodiment of the cap 140 of FIG. 5B, when the handle 165 is rotated about 180 degrees from the closed state, the rotation stop protrusion 167 may be engaged with the rotation stop rib 168 (also shown in FIG. 2). The rotation stop protrusion 167 can engage with the rotation stop rib 168 to provide a tactile feedback to the user that the cap 140 is in a full open state. In some embodiments, the rotation stop protrusion 167 and the rotation stop rib 168 may be of any suitable configuration. For example, the rotation stop protrusion 167 can be a deflectable lever that is captured between two rotation stop ribs 168 to prevent the handle 165 from further rotation. In this embodiment, the rotation stop protrusion 167 may be deflected by the user to allow the handle 165 to be rotated in either direction.

Further rotation of the handle 165 may cause the rotation stop protrusion 167 to be deflected by the rotation stop rib 168 and allow the sealing member 160 to be removed from the cap 140 as shown in FIG. 5C. In some embodiments, when the sealing member 160 is removed from the cap 140, drainage fluid within the container 110 can be poured out through the body 141 of the cap 140.

FIG. 6 illustrates the vacuum drainage collection bottle 100 with a drainage tube 102 coupled to the external connector 144 of the inlet 142. The drainage tube 102 may include a roller clamp 103 configured to be adjusted to control fluid flow through the drainage tube 102 and into the vacuum drainage collection bottle 100. In some embodiments, a connector 104 of any suitable type may be coupled to a distal end of the drainage tube 102 to allow the drainage tube 102 to be coupled to a drainage catheter inserted into a patient. For example, the connector 104 may be a universal connector (e.g., a Luer connector), a barbed connector, a connector to actuate a needleless connector (e.g., an Aspira connector), etc.

In use, the vacuum drainage collection bottle 100 may be used to drain fluid from a body cavity, such as the abdomen or the thorax, under vacuum. In some embodiments, the vacuum drainage collection bottle 100 may be provided to the user, health care professional, or patient with a vacuum or negative gauge pressure within the vacuum drainage collection bottle 100. The broad base 122 of the vacuum drainage collection bottle 100 can be disposed on a flat surface to prevent tipping of the vacuum drainage collection bottle 100. One end of the drainage tube 102 can be coupled to the external connector 144 of the inlet 142 and an opposite end can be coupled to an access device (e.g., needle or catheter) disposed within the body cavity to be drained.

In certain embodiments, the handle 165 may be rotated in a first direction about 180 degrees to transition the vacuum drainage collection bottle 100 from a closed state to an open state where drainage fluid flows freely into the container 110 of the vacuum drainage collection bottle 100, which can be caused at least in part by the vacuum or negative gauge pressure within the vacuum drainage collection bottle 100. In certain other embodiments, the handle 165 may be rotated until the user feels tactile feedback when the rotation stop protrusion 167 engages with the rotation stop rib 168. In some embodiments, the handle 165 may be rotated less than 180 degrees to reduce the flow rate of the drainage fluid into the container 110. In other embodiments, the handle 165 can be rotated in a second direction, opposite the first direction, to transition the vacuum drainage collection bottle 100 from the open state to the closed state. The handle 16 can thereafter be rotated in the first and/or second direction as desired to transition the vacuum drainage collection bottle 100 from the closed state to the open state, and back to the closed state. This may be done to provide intermittent drainage and allow the user to stop the drainage procedure when needed.

In some embodiments, when the drainage procedure is complete, the handle 165 may be further rotated in the first direction to remove the sealing member 160 from the cap 140. In other embodiments, the rotation stop protrusion 167 may be deflected by the rotation stop rib 168 to allow further rotation of the handle 165. When the sealing member 160 is removed from the cap 140, drainage fluid collected within the container 110 may be poured out of the container 110 through the cap 140. In certain embodiments, the cap 140 may include a spout or lip to prevent the drainage fluid from dripping or dribbling from the cap 140.

FIG. 7 depicts an embodiment of a vacuum drainage collection bottle 200 that resembles the vacuum drainage collection bottle 100 described above in certain respects. Accordingly, like features are designated with like reference numerals, with the leading digit incremented to "2." For example, the embodiment depicted in FIG. 7 includes a cap 240 that may, in some respects, resemble the cap 140 of FIG. 1. Relevant disclosure set forth above regarding similarly identified features thus may not be repeated hereafter. Moreover, specific features of the vacuum drainage collection bottle 100 and related components shown in FIGS. 1-6 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vacuum drainage collection bottle 200 and related components depicted in FIG. 7. Any suitable combination of the features, and variations of the same, described with respect to the vacuum drainage collection bottle 100 and related components illustrated in FIGS. 1-6 can be employed with the vacuum drainage collection bottle 200 and related components of FIG. 7, and vice versa. This pattern of disclosure applies equally to further embodiments depicted in subsequent figures and described hereafter, wherein the leading digits may be further incremented FIG. 7 is a perspective view of a body 241 of a cap 240 in accordance with another embodiment of a vacuum drainage collection bottle 200. As shown in FIG. 7, in some embodiments the inlet 242 includes a barbed external connector 244 for coupling to a drainage tube. The body 241 further includes internal threads 245 configured to threadingly engage with external threads of the sealing member. FIG. 7 further depicts a rotation stop rib 268 disposed on the body 241 that is configured to engage a rotation stop protrusion of a handle. This rotation stop rib 268 can be disposed at various locations along the body 241 of the cap 240 as desired.

FIG. 8 illustrates another embodiment of a vacuum drainage collection bottle 300 with a drainage tube 302 coupled to a female Luer connector 344 of an inlet 342 of a cap 340. The drainage tube 302 may include a roller clamp 303 configured to be adjusted to control fluid flow through the drainage tube 302 and a container 310. The drainage tube 302 further includes a male Luer connector 305 disposed at a proximal end of the drainage tube 302 to allow the drainage tube 302 to be coupled to the female Luer connector 344. The drainage tube 302 further includes a male Luer connector 304 disposed at a distal end of the drainage tube 302 to allow the drainage tube 302 to be coupled to a female Luer connector of a drainage catheter that is inserted into a patient. In some embodiments, the male Luer connectors 304, 305 are male Luer lock connectors. In other embodiments, the male Luer connectors 304, 305 are male Luer slip connectors. Other types of connectors can also be used.

Figure 9A:
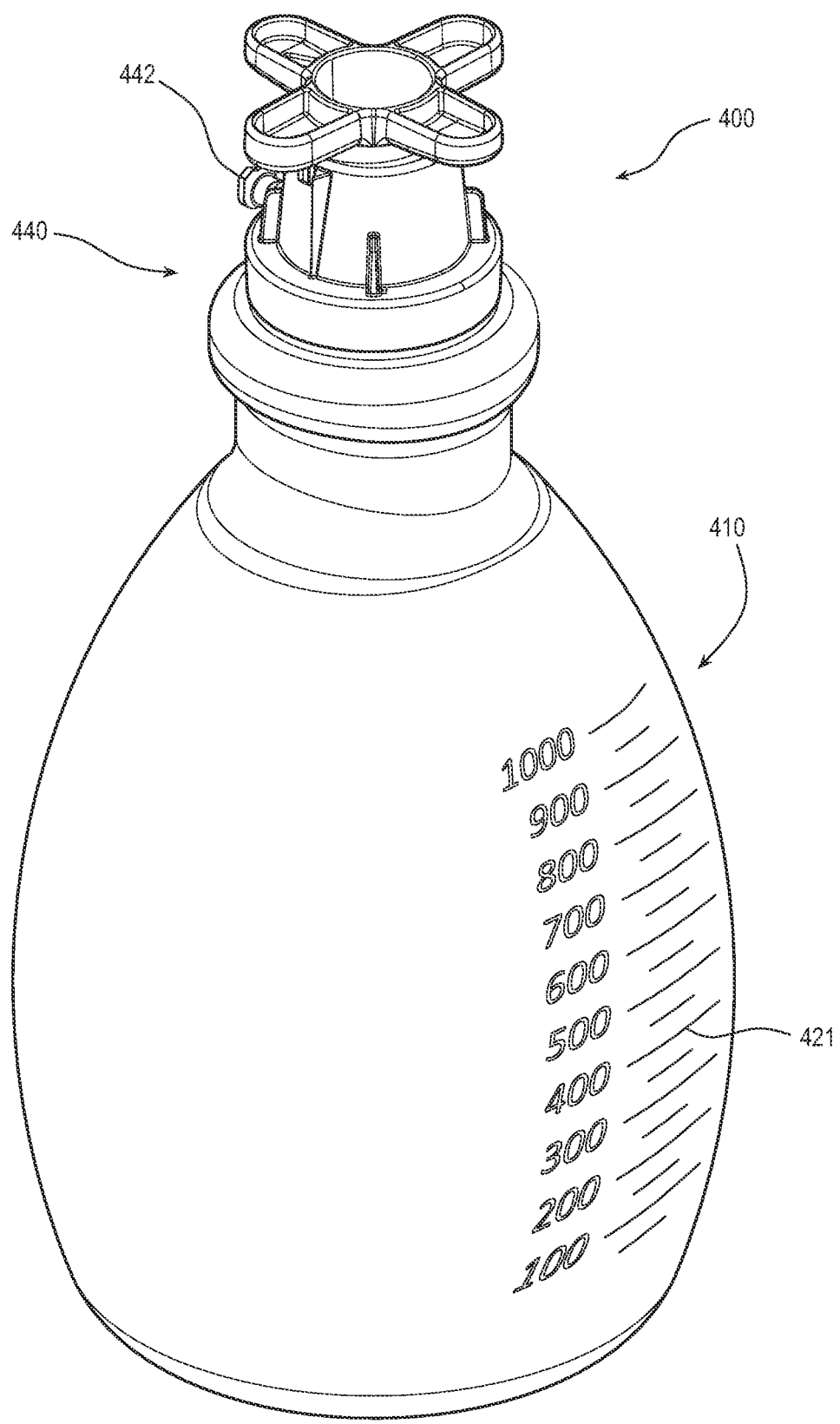
FIG. 9A is a perspective view of another embodiment of a vacuum drainage collection bottle.
Figure 9B:
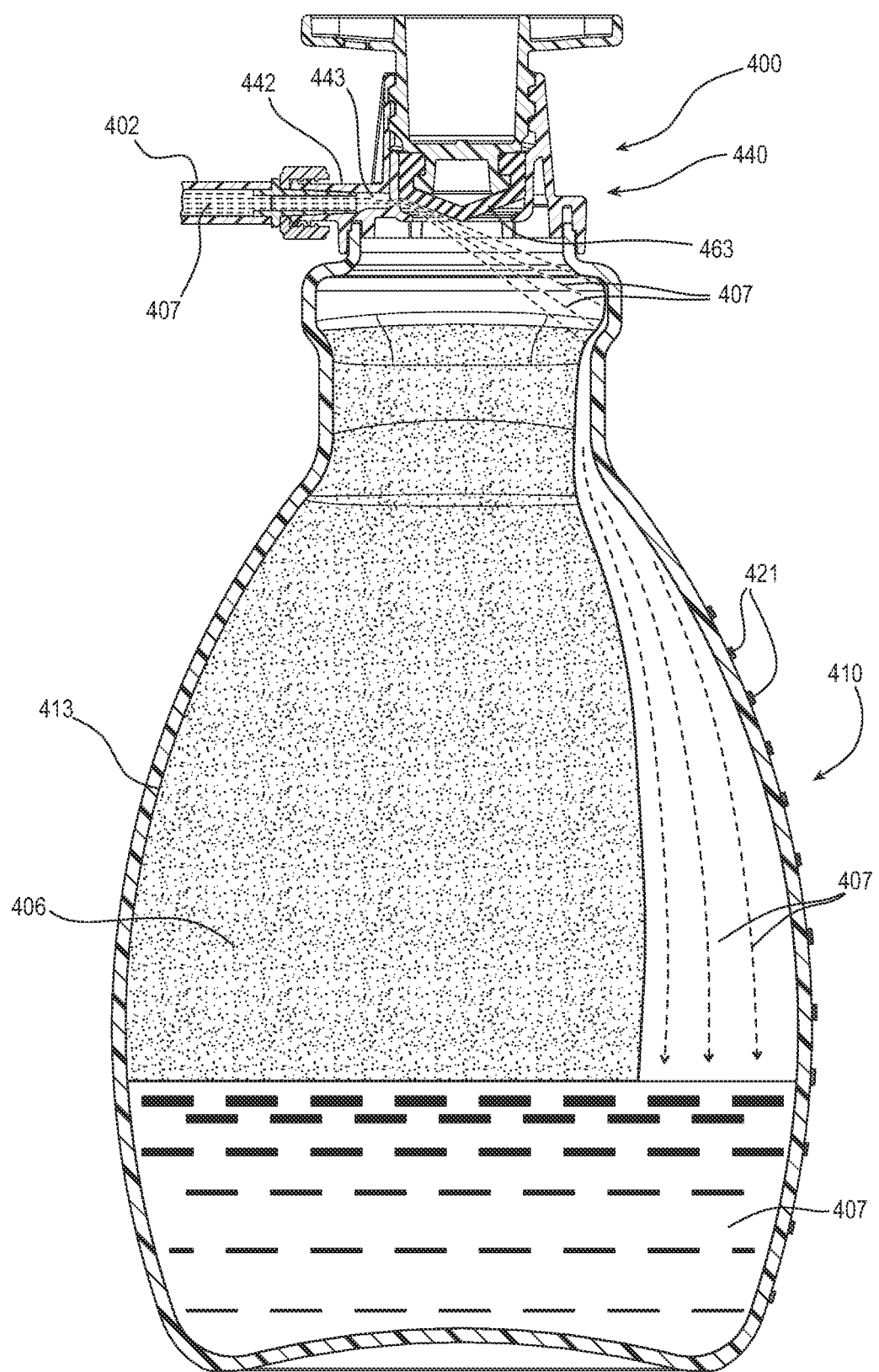
FIG. 9B is a cross-sectional side view of the vacuum drainage collection bottle of FIG. 9A showing clearing of condensation from an interior wall of a container.

FIGS. 9A and 9B illustrate another embodiment of a vacuum drainage collection bottle 400. As illustrated in FIGS. 9A and 9B, the vacuum drainage collection bottle 400 includes a cap 440 having an inlet 442 and a container 410 having indicia 421 to indicate a fluid volume within the container 410. In certain embodiments, the indicia can include a high contrast or dark color (e.g., black or blue) such that the indicia 421 can be easily visualized to determine a volume of drainage fluid 407 collected within the container 410. In some embodiments, the indicia 421 may be disposed on an exterior surface of the container 410 using any suitable technique, such as laser printing, transfer printing, embossing, decals, shrink sleeve, etc.

In some embodiments, when the drainage fluid 407 fills or enters the container 410, condensate 406 forms or is otherwise disposed on an inner surface 413 of the container 410 due to a difference in a temperature of the drainage fluid 407 (e.g., about 37 degrees Celsius or approximate body temperature) and a temperature of the inner surface 413 of the container 410 (e.g., about 22 degrees Celsius or approximate room temperature). The condensate 406 may fog the inner surface 413 and can inhibit or reduce visualization of the level of the drainage fluid 407 relative to the indicia 421.

In the illustrated embodiment, the inlet 442 is oriented approximately 180 degrees from or opposite of the indicia 421. In other embodiments, the inlet 442 can be oriented between about 130 degrees and about 230 degrees, or between about 150 degrees and about 210 degrees from the indicia 421. In this orientation, the flow of drainage fluid 407 can be directed towards an inner surface 410 of the container that is opposite the inlet 442 and/or adjacent where the indicia 421 is disposed. For instance, as shown in FIG. 9B, during use a drainage tube 402 is coupled to the inlet 442. Drainage fluid 407 is drawn through the drainage tube 402 and the fluid channel 443 of the inlet 442 by the vacuum or negative gauge pressure of the container 410. When the drainage fluid 407 enters the container 410, it may be sprayed, flow, or otherwise directed to an inner surface 413 of the container 410 opposite the inlet 442 (e.g., about 180 degrees from the inlet 442) and/or adjacent where the indica 421 is disposed. In certain embodiments, the drainage fluid 407 is also directed downwards and towards the inner surface 413 of the container 410 by the stopper 463.

As further shown in FIG. 9B, after the drainage fluid 407 contacts the inner surface 413 it may flow down the inner surface 413 adjacent the indicia 421. As the drainage fluid 407 flows down the inner surface 413, the condensate 406 can be cleared from the inner surface 413 allowing for an unobstructed visualization of the level of the drainage fluid 407 within the container 410 relative to the indicia 421. This is illustrated in FIG. 9B which depicts the condensate 406 having been cleared from a portion of the inner surface 413 by the flow of drainage fluid 407 relative to the remaining portion of the inner surface 413 of the container 410.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of draining a body cavity may include one or more of the following steps: inserting an access device into a cavity of a patient's body; coupling a drainage tube to the access device and to an inlet of a drainage collection bottle; gripping an ergonomic shaped neck portion of the drainage collection bottle; and displacing a sealing member of the drainage collection bottle to transition the fluid collection bottle from a closed state to an open state. One or more additional steps can also be employed, such as displacing the sealing member to transition the fluid collection bottle from the open state to the closed state; partially displacing the sealing member from the drainage collection bottle closed state to control a rate of fluid flow into the drainage collection bottle; and/or removing the sealing member from the fluid collection bottle; and emptying the fluid collection bottle. Other steps are also contemplated.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A drainage collection bottle, comprising:
a container comprising:
a body portion; and
a neck portion, wherein the neck portion comprises a shape configured for ergonomic gripping of the neck portion, wherein the shape of the neck portion is a non-circular, oval, or elliptical cross-sectional shape having a primary axis length greater than a secondary axis length, and wherein the neck portion includes a region throughout which the primary axis length and the secondary axis length are constant; and
a cap coupled to the container and comprising an inlet configured to receive drainage fluid into the drainage collection bottle, the cap being configured to selectively transition the drainage collection bottle between a closed state preventing fluid communication between the inlet and the body portion and an open state allowing fluid communication between the inlet and the body portion, wherein the cap comprises:
a body comprising the inlet; and
a sealing member configured to selectively seal and unseal the inlet, wherein the sealing member comprises:
a threaded plunger configured to threadedly engage with the body;
a stopper disposed at an end of the plunger, wherein the stopper is configured to selectively seal and unseal the inlet; and
a handle disposed at an end of the plunger opposite the stopper;
wherein the handle is configured to rotate the plunger to selectively move the plunger relative to the inlet to transition the drainage collection bottle between the closed state and the open state.

2. The drainage collection bottle of claim 1, wherein a ratio of the primary axis length to the secondary axis length ranges from 1.05:1 to 1.35:1.

3. The drainage collection bottle of claim 1, further comprising:
a circular flange configured for ergonomic support of the drainage collection bottle and positioned with the neck portion between the flange and the body portion; and
a rim positioned with the flange between the rim and the neck portion, wherein the cap is sealingly coupled to the container at the rim.

4. The drainage collection bottle of claim 1, wherein the body portion comprises a truncated prolate spheroid shape comprising a closed base disposed opposite the neck portion.

5. The drainage collection bottle of claim 1, wherein the handle comprises one or more arms extending radially outward from a central axis of the plunger.

6. The drainage collection bottle of claim 1, wherein the handle comprises an indicium to indicate whether the cap is in a closed state or an open state.

7. The drainage collection bottle of claim 1,
wherein when the drainage collection bottle is in the closed state the stopper seals the inlet to prevent fluid from passing through the inlet into the container; and
wherein when the drainage collection bottle is in the open state the stopper is disposed within the cap such that fluid is allowed to flow through the inlet into the container.

8. The drainage collection bottle of claim 1, wherein the body further comprises a rotation stop rib and the handle comprises a rotation stop protrusion configured to engage the rotation stop rib to provide a tactile feedback to a user to indicate that the drainage collection bottle is in the open state.

9. The drainage collection bottle of claim 1, further comprising:
indicia for indicating a volume of collected drainage fluid, wherein the indicia is disposed on the body portion of the container, and wherein the cap is coupled to the container such that the inlet is opposite the indicia.

10. The drainage collection bottle of claim 1, further comprising a shrink sleeve applied to the container, wherein the shrink sleeve comprises indicia for indicating a volume of collected drainage fluid.

11. The drainage collection bottle of claim 1, further comprising a vacuum within the container when the drainage collection bottle is provided to a user.

12. A method of draining fluid from a body cavity, comprising:
inserting an access device into a cavity of a body;
coupling a drainage tube to the access device and to an inlet of a cap of a drainage collection bottle having a body portion, wherein the drainage collection bottle comprises a vacuum;
gripping an ergonomic shaped neck portion of the drainage collection bottle, wherein the shape of the neck portion is a non-circular, oval, or elliptical cross-sectional shape having a primary axis length greater than a secondary axis length, and wherein the neck portion includes a region throughout which the primary axis length and the secondary axis length are constant; and
displacing a sealing member of the drainage collection bottle to transition the drainage collection bottle between a closed state preventing fluid communication between the inlet and the body portion and an open state allowing fluid communication between the inlet and the body portion, wherein the sealing member comprises:
a threaded plunger configured to threadedly engage with a body of the cap;
a stopper disposed at an end of the plunger, wherein the stopper is configured to selectively seal and unseal the inlet; and
a handle disposed at an end of the plunger opposite the stopper, wherein the handle is configured to rotate the plunger to selectively move the plunger relative to the inlet to transition the drainage collection bottle between the closed state and the open state.

13. The method of claim 12, wherein the ergonomic shaped neck portion comprises an oval shape and a flange.

14. The method of claim 12, further comprising:
removing the sealing member from the drainage collection bottle; and
emptying the fluid collection bottle.

15. The method of claim 12, further comprising displacing the sealing member to transition the drainage collection bottle from the open state to the closed state.

16. The method of claim 12, further comprising coupling a male Luer connector disposed at a proximal end of the drainage tubing to a female Luer connector of the inlet and coupling a male Luer connector disposed at a distal end of the drainage tubing to a female Luer connector of a drainage catheter.

17. The method of claim 12, further comprising:
drawing drainage fluid into the drainage collection bottle, wherein the drainage fluid is directed onto an interior surface of the drainage collection bottle, wherein volume indicia are disposed adjacent the interior surface, and wherein condensate is cleared from the interior surface when the drainage fluid flows along the interior surface.

18. A drainage collection system, comprising: a drainage collection bottle, comprising:
a container comprising:
a drainage containment portion; and
an open neck portion, wherein the neck portion comprises a shape configured for ergonomic gripping of the neck portion, wherein the shape of the neck portion is a non-circular, oval, or elliptical cross-sectional shape having a primary axis length greater than a secondary axis length, and wherein the neck portion includes a region throughout which the primary axis length and the secondary axis length are constant; and
a cap coupled to the container and comprising an inlet configured to receive drainage fluid into the container, the cap being configured to selectively transition the drainage collection bottle between a closed state preventing fluid communication between the inlet and the drainage containment portion and an open state allowing fluid communication between the inlet and the drainage containment portion, wherein the cap comprises:
a body comprising the inlet; and
a sealing member configured to selectively seal and unseal the inlet, wherein the sealing member comprises:
a threaded plunger configured to threadedly engage with the body;
a stopper disposed at an end of the plunger, wherein the stopper is configured to selectively seal and unseal the inlet; and
a handle disposed at an end of the plunger opposite the stopper;
wherein the handle is configured to rotate the plunger to selectively move the plunger relative to the inlet to transition the drainage collection bottle between the closed state and the open state; and
a drainage tube coupled to the inlet of the cap and in fluid communication with the container comprising:
a male Luer connector disposed at a proximal end and coupled to the inlet; and
a male Luer connector disposed at a distal end.

19. The drainage collection system of claim 18, wherein the inlet comprises a female Luer connector.

20. The drainage collection system of claim 18, further comprising a drainage catheter coupled to the male Luer connector disposed at the distal end of the drainage tube.

* * * * *